United States Patent [19]

Yoshida

[11] Patent Number: Plant 6,252

[45] Date of Patent: Aug. 16, 1988

[54] AFRICAN VIOLET NAMED ARCTIC SNOW

[76] Inventor: Eiichi Yoshida, P.O. Box 4836, Hayward, Calif. 94540

[21] Appl. No.: 911,641

[22] Filed: Sep. 24, 1986

[51] Int. Cl.[4] ..... A01H 5/00

[52] U.S. Cl. ..... Plt./69

[58] Field of Search ..... Plt./69

*Primary Examiner*—Robert E. Bagwill

[57] ABSTRACT

A new variety of African violets that have been bred from a hybrid formed by crossing *Saintpaulia ionantha,* the traditional florists' African violet with the high altitude species, *Saintpaulia schumensis.* The high cost of energy in northern latitudes and the relatively high temperatures required by *Saintpaulia ionantha,* which grows naturally at the foot of Mount Usamabara in East Africa, have made commercial growing of the violet expensive. By bringing in genes from *Saintpaulia schumensis* which grows at some 7,000 feet on the same mountain, where temperatures can fall as low as 55 degrees Fahrenheit, a new avenue of growth is opened up for this popular plant.

1 Drawing Sheet

BACKGROUND OF THE NEW PLANT

To obtain this new variety of African violet plant, the inventor cross-pollenated the seed parent S. 'Optimara Linda' and the pollen parent *S. schumensis*×S. 'Optimara Georgia'. The seed pods of the pollenated plants were used as the generic basis for initiating further experimental series. Approximately 25 seedlings were selected by very rigid standards for further propagation. Propagation of these plants and refinement out of limited selected plants continued and tests were conducted for the development of permanent characteristics of disease resistance and vigorous growth.

DESCRIPTION OF THE PLANT

Sheet one is a full color photographic view of the plant in bloom; the colors shown being as nearly true as it is reasonably possible to obtain by conventional photographic procedures.

The following is a detailed description of my new African violet plant with the color designation being accorded to the R.H.S. Colour Chart published by The Royal Horticultural Society of London, England, with collaboration by the British Colour Council.

DETAILED DESCRIPTION

Plant:

*Name.*—Arctic Snow.

*Botanical classification.*—*Saintpaulia ionantha.*

*Commercial classification.*—African violet.

*Origin.*—Hybrid.

*Seed parent.*—S. 'Optimara Linda'.

*Pollen parent.*—*S. schumensis*×S. 'Optimara Georgia'.

*Form.*—Rosette arrangement.

*Height.*—6–10 cm.

*Growth.*—Moderate, petioles at first upright, becoming horizontal with age.

*Size.*—Medium, to 20 cm in diameter.

*Mutation prone.*—Slight.

Leaves:

*Shape.*—Ovate, margins v. slightly crenate.

*Length.*—6–7 cm on mature leaves.

*Width.*—5–6 cm on mature leaves.

*Color.*—Upperside: Light green. Underside: Pale Green.

*Texture.*—Upperside: Moderately hairy. Underside: Hairy.

*Ribs and veins.*—Moderately pronounced, pinnate, greenish below.

*Petiole.*—Flattened at base, moderately hairy, green.

Flowers:

*Blooming habit.*—Continuous and abundant under optimal growing conditions.

*Number.*—3–10 per peduncle.

*Size.*—3–4 cm in diameter.

*Color.*—White (RHS 155C).

*Type.*—Single, violet-like.

*Petals.*—5, with 0 to 4 petaloids, edges entire.

*Texture.*—Smooth, slightly flexible.

*Appearance.*—Upperside smooth, lower side slightly pubescent.

*Peduncles.*—7–8 cm in height, moderately hairy, greenish.

*Inflorescence.*—Cyme, upright, above the foliage.

*Calyx.*—Quinquepartite, green, moderately hairy.

*Persistence.*—Flowers do not drop.

*Fragrance.*—None.

Reproductive organs:

*Stamens.*—Two, occasionally fused with petaloids. Anthers: Bright yellow, two per filament. Filaments: c. 0.5 cm in length. Pollen: Light yellow.

*Pistils.*—One. Stigma: Visible and accessible, becoming swollen when receptive and exuding a droplet of clear liquid. Style: c. 0.5 cm in length. Ovary: Superior.

Other characteristics: This variety will grow at lower temperatures than most commercially available hybrids because of its *Saintpaulia schumensis* parentage.

I claim:

1. An African violet plant as shown and described.

500
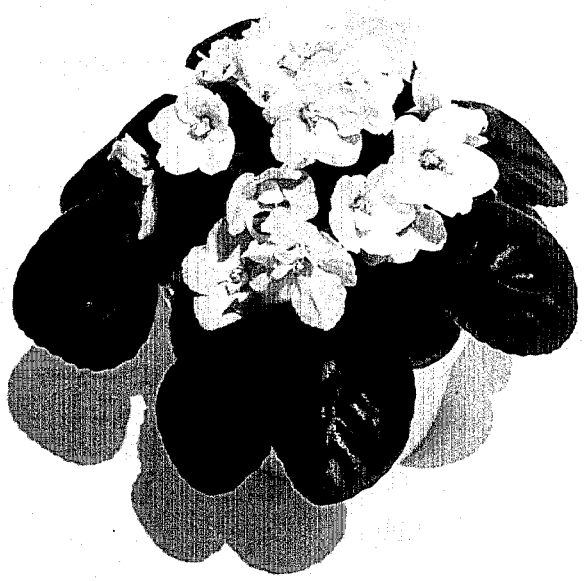

* * * * *